United States Patent [19]

Scott et al.

[11] Patent Number: 5,006,252

[45] Date of Patent: Apr. 9, 1991

[54] PURIFIED PROTEASE NEXIN

[75] Inventors: Randy W. Scott, Sunnyvale; Joffre B. Baker, El Granada, both of Calif.

[73] Assignees: Invitron, St. Louis, Mo.; University of Kansas, Lawrence, Kans.

[21] Appl. No.: 378,434

[22] Filed: Jul. 10, 1989

Related U.S. Application Data

[63] Continuation of Ser. No. 871,501, Jun. 6, 1986, abandoned, which is a continuation-in-part of Ser. No. 870,232, Jun. 3, 1986, abandoned.

[51] Int. Cl.$^5$ .............................................. B01D 15/08
[52] U.S. Cl. .................................... 210/635; 210/656; 530/413; 530/417
[58] Field of Search ............ 210/635, 636, 659, 198.2, 210/502.1; 530/413, 417

[56] References Cited

PUBLICATIONS

Scott, Protease Nexin, The Journal of Biological Chemistry, vol. 260, No. 11, Jun. 10, 1985, pp. 7029-7034.
Scott, Purification of Human Protease Nexin, vol. 258, No. 17, Sep. 10, 1983, pp. 10439-10444.
Scott, R. W., Chemical Abstracts, 103, No. 3 (1985), "Protease Nexin, Properties and Modified Purification Procedure".
Eaton, D. L., Chemical Abstracts, 101, No. 7 (1984), "Purification of Human Fibroblast Urokinase Proenzyme and Analysis of Its Regulation by Proteases and Protease Nexin".
Gloor, S., Biological Abstracts, 83, No. 7 (1987), "A Glia-Derived Neurite Promoting Factor with Protease Inhibitory Activity Belongs to the Protease Nexins".
Erickson, L. A., Proc. Natl. Acad. Sci., 82: 8710-8714 (1985), "The Primary Plasminogen-Activator Inhibitors in Endothelial Cells, Platelets, Serum, and Plasma are Immunologically Related".
Ny, T. et al, Proc. Natl. Acad. Sci., 83:6776-6780 (1986), "Cloning and Sequence of a cDNA Coding for the Human Beta-Migrating Endothelial-Cell-Type Plasminogen Activator Inhibitor".
Proteases in Biological Control (1975), Reich et al., eds., Cold Spring Harbor, New York, pp. 1-10 (1975).
Jones et al. (1980), Cancer Research 40:3222-3227, "Destruction of Extracellular Matrices Containing Glycoproteins".
Bergman et al. (1986), Proc. Natl. Acad. Sci., U.S.A., 83:996-1000, "Inhibition of Tumor-Cell-Mediated Extracellular Matrix".
McGuire-Goldring et al. (1984), Arth. Rheum., 27:S24, Abstract 51.
Monrad et al. (1983), Prog. Brain Res., 58:359-364, "Inhibition of Protease Activity Can Lead to Neurite Extension".

Primary Examiner—Ernest G. Therkorn
Attorney, Agent, or Firm—Irell & Manella

[57] ABSTRACT

The gene encoding protease nexin I (PN-I) is cloned and expressed to provide practical quantities of PN-1 for diagnostic and therapeutic use. PN-I is a serine protease inhibitor useful in controlling conditions mediated by proteolytic activity.

5 Claims, 4 Drawing Sheets

```
-150            -140            -130            -120            -110            -100
 *               *               *               *               *               *
TTC CGG cTG GTG AAC CCT CCT CGC CGC CGC CGC TTC GTT CCG TCC TCG GAC TCC CCG CGC

-90             -80             -70             -60             -50             -40
 *               *               *               *               *               *
CGC CGA GAC nAG GCT CCC GCT CCG GTT GCC GCC CGC ACC GCC TCC GCG CCC CCT GGG ATC

-30             -20             -10              1              10              20              30
 *               *               *               *               *               *               *
CAG CGA GCG TCG TCC TTG GTG GAA GGA ACC ATG GAA TTG GCA TCT CCC CCT CTT CCT CTT
                                             Met Glu Leu Ala Ser Pro Pro Leu Pro Leu 40              50              60              70              80              90
                  *               *               *               *               *               *
GCC TCT GTG ACG CTG CCT TCC ATC TGC TCC CAC TTC AAT CCT CTG TCT CTC GAG GAA CTA
Ala Ser Val Thr Leu Pro Ser Ile Cys Ser His Phe Asn Pro Leu Ser Leu Glu Glu Leu 100             110             120             130             140             150
                  *               *               *               *               *               *
GGC TCC AAC ACG GGG ATC CAG GTT TTC AAT CAG ATT GTG AAG TCG AGG CCT CAT GAC AAC
Gly Ser Asn Thr Gly Ile Gln Val Phe Asn Gln Ile Val Lys Ser Arg Pro His Asp Asn

ATC GTG ATC
Ile Val Ile
```

FIG. 1a

```
                         20              24
AMINO ACID          Phe Asn Gln Ile Val
CODON         5'    TTT AAT CAA ATT GT    3'
                     C   C   G   C
                                 A
```

REVERSE COMPLEMENT 14MER:

```
              5'   ACAATTTGATTAAA   3'
                    G   C   G  G
                    T
```

FIG. 1b

AMINO ACID SEQUENCE:

```
    14                              20                    25
   Asn Thr Gly Ile Gln Val Phe Asn Gln Ile Val Lys
```

CONSENSUS 36MER:

```
    1                12              24              36
5' AAC ACC GGC ATC CAG GTG TTC AAT CAG ATC GTG AAG  3'
    T   T                                   T   C
```

FIG.2

```
-150         -140         -130         -120         -110         -100
  *            *            *            *            *            *
TTC CGG cTG GTG AAC CCT CCT CGC CGC CGC TTC GTT CCG TCC TCG GAC TCC CCG CGC

-90          -80          -70          -60          -50          -40
  *            *            *            *            *            *
CGC CGA GAC nAG GCT CCC GCT CCG GTT GCC ACC CGC GCC CGC GCC TCC GCG CCC CCT GGG ATC

-30          -20          -10            1           10           20           30
  *            *            *            *            *            *            *
CAG CGA GCG TCG TCC TTG GTG GAA GGA ACC ATG GAA TTG GCA TCT CCC CCT CTT CCT CTT
                                            Met Glu Leu Ala Ser Pro Pro Leu Pro Leu

40           50           60           70           80           90
             *            *            *            *            *            *
GCC TCT GTG ACG CTG CCT TCC ATC TGC TCC CAC TTC AAT CCT CTG TCT CTC GAG GAA CTA
Ala Ser Val Thr Leu Pro Ser Ile Cys Ser His Phe Asn Pro Leu Ser Leu Glu Glu Leu 100          110          120          130          140          150
             *            *            *            *            *            *
GGC TCC AAC ACG GGG ATC CAG GTT TTC AAT CAG ATT GTG AAG TCG AGG CCT CAT GAC AAC
Gly Ser Asn Thr Gly Ile Gln Val Phe Asn Gln Ile Val Lys Ser Arg Pro His Asp Asn

ATC GTG ATC
Ile Val Ile
```

NORTHERN HYBRIDIZATION OF pN-18 CLONE

RNA SAMPLES WERE DENATURED AND FRACTIONED ON A METHYL MECURY AGAROSE GEL WHICH WAS ELECTROPHORETICALLY TRANSFERED TO A GENESCREEN MEMBRANE FILTER. THE pN-18 PROBE WAS PREPARED BY PRIMER EXTENSION OF TEH M-13 CLONE IN THE PRESENCE OF 32PdCTP. THE RNA FILTER WAS HYBRIDIZED IN FORMAMIDE HYBRIDIZATION BUFFER (50% FORMAMIDE; 5XSSC, 2X DENHARDTS, 20mM SODIUM PHOSPHATE BUFFER pH7, 0.2% SDS, AND 100ug/ml YEAST RNA) AT 42'C FOR 36 HOURS WITH 2X10*7 cpm OF 32P LABELED PROBE. THE FILTER WAS WASHED AT 42'C IN 2XSSC CONTAINING 0.2% SDS AND EXPOSED TO X-RAY FILM.

LANE 1)   1ug HUMAN FIBROBLAST NON-polyA RNA.
LANE 2)   6ug HUMAN FIBROBLAST polyA-RNA 1-23.
LANE 3)   8ug HUMAN FIBROBLAST polyA-RNA 1-6.
LANE 4)   8ug HUMAN 293 CELLS polyA-RNA.
LANE 5)   8ug BOWES MELANOMA polyA-RNA.
LANE 6)   5ug SK HEPATOMA NON-polyA RNA.

PURIFIED PROTEASE NEXIN

This is a continuation of application U.S. Ser. No. 871,501, filed June 6, 1986, which, in turn, is a continuation-in-part of parent application, U.S. Ser. No. 870,232, filed June 3, 1986 and, both now abandoned.

TECHNICAL FIELD

The invention relates to recombinant production of cardiovascular pharmaceuticals. In particular, it concerns the cloning and expression of the gene for protease nexin I (PN-I).

BACKGROUND ART

Connective tissue cells secrete protease inhibitors which are specific for serine proteases. Since serine proteases are involved in development and migration of cells, regulation of the activity of these enzymes is necessary to exercise control over the remodeling or destruction of tissues (*Proteases in Biological Control* (1975), Reich, E., et al, eds., Cold Spring Harbor, N.Y.). The inhibitors designated protease nexins irreversibly bind to serine proteases at their catalytic sites (Baker, J.B., et al, *Cell* (1980) 21:37–45) and effect the clearance of the bound proteases via receptor-mediated endocytosis and lysosomal degradation (Low, D. A., et al, *Proc Natl Acad Sci* (USA) (1981) 78:2340–2344; Baker, J. B., et al, in *The Receptors* 3 (1985), Conn, P. M., ed, Academic Press, in press).

Three protease nexins have been identified. Protease nexin I (PN-I) has been purified from serum-free medium conditioned by human foreskin cells (Scott, R. W., et al, *J Biol Chem* (1983) 58:10439–10444). It is a 43 kd glycoprotein which is released by fibroblasts, myotubes, heart muscle cells, and vascular smooth muscle cells. Its release, along with that of plasminogen activator, is stimulated by phorbol esters and by mitogens (Eaton, D. L., et al, *J Cell Biol* (1983) 123:128). Native PN-I is an approximately 400 amino acid protein containing about 6% carbohydrate. Since it is present only in trace levels in serum, it apparently functions at or near the surfaces of interstitial cells. PN-I inhibits all the known activators of urokinase proenzyme, plasmin, trypsin, thrombin, and factor Xa (Eaton, D. L., et al, *J Biol Chem* (1984) 259:6241). It also inhibits tissue plasminogen activator and urokinase.

The need for practical amounts of purified PN-I is severalfold. First, PN-I has clear utility as a pharmaceutical for conditions characterized by excess amounts of urokinase and tissue plasminogen activator, or as an antidote for overdoses of these enzymes as agents for solution of blood clots. Indications which are clearly susceptible to PN-I treatment include the autoimmune disease penphigus, which is an extremely common disease in dogs, and psoriasis, which is believed to be due to an overproduction of plasminogen activator. Second, because the role of PN-I in regulating various developmental stages of tissue formation and remodeling is relatively complex, it would be desirable to be able to use model systems to demonstrate in greater detail the role PN-I plays. This can be done effectively only if practical quantities are available. Finally, PN-I is useful as an assay reagent in immunological assays for its levels in serum or in other tissues or for other biological assays.

Exemplary of the conditions for which further study of the role of PN-I is desirable are tumor metastasis, wound healing, and inflammation. In tumor metastasis, malignant cells must penetrate the extracellular matrix laid down by vascular smooth muscle cells, a process which is mediated by secreted plasminogen activator. In the model system of Jones, P. A., et al, *Cancer Res* (1980) 40:3222, an in vitro system based on the invasion of the extracellular matrix by human fibrosarcoma cells, it could be shown that PN-I at 0.1 μM causes virtually complete suppression of the invasion (Bergman, B. L., et al, *Proc Natl Acad Sci* USA (1986) 83:996–1000. The proteolytic activity of thrombin, which is a fibroblast mitogen important in wound healing, is effective only when added to cultures at concentrations above the concentrations of secreted PN-I (Baker, J. B., et al, *J Cell Physiol* (1982) 112:291; Low, D. A., et al, *Nature* (1982) 298:2476). It has been suggested that PN-I has an antiinflammatory function, since PN-I secretion by synovial fibroblasts increases dramatically when the cells are treated with interleukin-I (McGuire-Goldring et al., *Arth Rheum* (1984) 27:S24). PN-I may also have a neurological function, since a similar inhibitor which stimulates neurite extension has been shown to be secreted from glial cells (Monard et al, *Prog Brain Res* (1983) 58:359).

Elucidation of the precise function of PN-I in any of the foregoing would be greatly simplified by the availability of the needed amounts of pure material. These amounts are also needed for use in PN-I as a pharmaceutical and in diagnosis and assay. The present invention provides a solution to the problem of obtaining sufficient quantities of PN-I, as well as a mechanism for modifying PN-I structure in order to make it more effective.

DISCLOSURE OF THE INVENTION

The invention provides purified PN-I protein, DNA coding sequence, expression systems, and methods which permit the production of recombinant mammalian PN-I. By employing these materials and methods, desired quantities of the PN-I protein can be produced, either in glycosylated or unglycosylated form, depending on the expression systems employed, and the gene can be modified, if desired, to alter the precise amino acid sequence so as to enhance the desired properties of the protein. This is all possible through the availability of the gene for human PN-I foreskin fibroblast cells, which is useful directly in producing the corresponding PN-I, and is also useful as a probe to retrieve the cDNA sequences encoding these genes in other species. In particular, retrieval of the murine sequence is desirable, as many model systems for providing a detailed description of the role of such factors are conveniently based on murine cells, tissues, or whole organisms.

Thus, in one aspect the invention relates to a DNA sequence encoding mammalian PN-I and to derivatives thereof, which can be expressed to obtain proteins with PN-I activity. In other aspects, the invention relates to cells transformed with this DNA sequence, and to the PN-I proteins produced by these cells. In addition, the invention relates to purified protein having the N-terminal sequence of the native protein as disclosed herein, to antibodies prepared by administration of the recombinant or purified native protein, and to DNA probes capable of retrieving PN-I cDNA.

MODES OF CARRYING OUT THE INVENTION

A. Definitions

As used herein, "protease nexin I" (PN-I) refers to a protein which is active in the standard diagnostic assays for PN-I, which are based on four criteria, as follows: (1) The protein complexes to thrombin: (2) this complexation is accelerated by heparin; (3) the protein must bind to the cell of its origin, for example, in this case to fibroblasts; and (4) heparin must inhibit this binding.

PN-I is distinguishable from the two other protease nexin factors, PN-II and PN-III (Knauer, D.J., et al, J Biol Chem (1982) 257:15098–15104), which are also major thrombin inhibitors, but are less strongly binding to this protease.

"Control sequence" refers to a DNA sequence or sequences which are capable, when properly ligated to a desired coding sequence, of effecting its expression in hosts compatible with such sequences. Such control sequences include at least promoters in both procaryotic and eucaryotic hosts, and preferably, transcription termination signals. Additional factors necessary or helpful in effecting expression may also be identified. As used herein, "control sequences" simply refers to whatever DNA sequence may be required to effect expression in the particular host used.

"Cells" or "cell cultures" or "recombinant host cells" or "host cells" are often used interchangeably as will be clear from the context. These terms include the immediate subject cell, and, of course, the progeny thereof. It is understood that not all progeny are exactly identical to the parental cell, due to chance mutations or differences in environment. However, such altered progeny are included in these terms, so long as the progeny retain the characteristics relevant to those conferred on the originally transformed cell. In the present case, for example, such a characteristic might be the ability to produce recombinant PN-I.

"Purified" or "pure" refers to material which is free from substances which normally accompany it as found in its native state. Thus "pure" PN-I refers to PN-I which does not contain materials normally associated with its in situ environment in human or other mammalian tissue. Of course, "pure" PN-I may include materials in covalent association with it, such as glycoside residues.

"Degenerate with", as referred to a DNA sequence, refers to nucleotide sequences encoding the same amino acid sequence as that referenced.

"Operably linked" refers to a juxtaposition wherein the components are configured so as to perform their usual function. Thus, control sequences or promoters operably linked to a coding sequence are capable of effecting the expression of the coding sequence.

B. General Description

PN-I was purified to homogeneity from serum-free medium conditioned by human foreskin fibroblasts in microcarrier cultures by affinity chromatography on heparin-agarose, followed by gelexclusion chromatography, as described in detail by Scott, R. W., et al, J Biol Chem (1985) 260:7029–7034, incorporated herein by reference. Protease nexin was purified from serumfree medium conditioned by human foreskin fibroblasts in microcarrier cultures, as previously described, [Scott (1983)supra], with the following modifications. Sodium chloride was added to the harvest buffer to bring the final NaCl concentration in medium plus buffer to 0.28M. Triton X-100 was omitted from the harvest buffer, and the harvested medium was filtered through a 45μ Millipore filter before carrying out protein concentration by (Amicon) hollow filter ultrafiltration. These steps extend the life of Amicon hollow fiber filters. The concentrated medium from a single 3 liter microcarrier culture was passed down a 0.7×30 cm heparin-agarose column that was preequilibrated with 0.3M NaCl, 20 mM sodium phosphate, and 0.02% sodium azide, pH 7.0. The column was rinsed with 50 ml of this buffer and then eluted at 6–9 ml/h using a linear gradient formed with 0.1 l of this buffer and 0.1 l of 1.0M NaCl, 20 mM sodium phosphate, and 0.02% azide, pH 7.0. Protease nexin eluted from this column in 0.55 0.6M NaCl (FIG. 1, upper panel). [in Scott (1985) at page 7030, column 2]. Protease nexin peak fractions, containing from 0.8 to 2 mg of protein, were placed in an $M_r = 12,000-14,000$ cutoff dialysis bag (Spectropore) and concentrated to 0.5 ml using Aquacide II (Calbiochem-Behring). A negligible amount of protein was lost during concentration by this method. The concentrated material, which contained protease nexin at 80–93% purity was stored at $-80°$ C. until further purification. The Scott (1985) article indicates a heparin-column resolves classes of protease nexin. Of course, other chromatographic supports which contain heparin for affinity binding can also be used. The purified protein shows an $M_r$ of 42–43 kd, based on sedimentation equilibrium analysis, or of 47 kd, estimated from gel-exclusion chromatography. The purified material shows the properties exhibited by PN-I when contained in conditioned medium, including formation of sodium dodecylsulfate-stable complexes with thrombin, urokinase, and plasmin; inhibition of protease activity; heparin-enhanced inhibition of thrombin; and cellular binding of protease-PN complexes in a heparin-sensitive reaction. The purified protein contains approximately 6% carbohydrate with 2.3% amino sugar, 1.1% neutral sugar, and 3.0% sialic acid. The N-terminal amino acid sequence of the isolated, purified protease nexin was determined for the first 34 amino acids to be: Ser-His-Phe-Asn-Pro-Leu-Ser-Leu-Glu-Glu-Leu-Gly-Ser-Asn-Thr-Gly- Ile-Gln-Val-Phe-Asn-Gln-Ile-Val-Lys-Ser-Arg-Pro-His-Asp-Asn-Ile- Val-Ile.

cDNA encoding the complete human PN-I protein was obtained from a foreskin fibroblast DNA library. The retrieval of this clone took advantage of probes based on the amino acid sequence determined in the native protein. The cloned cDNA is amenable to expression in recombinant cells of both procaryotic and eucaryotic organisms, as described above, by excising the coding sequence from the carrier vector and ligating it into suitable expression systems. The PN-I can be directly produced as a mature protein preceded by a Met N-terminal amino acid, which may or may not be processed, depending on the choice of expression systems, as a fusion protein to any desirable additional N-terminal or C-terminal sequence, or secreted as a mature protein when preceded by a signal sequence, either its own, or a heterologous sequence provided by, for example, the known signal sequence associated with the bacterial β-lactamase gene or with secreted human genes such as insulin or growth hormones. Means for providing suitable restriction sites at appropriate locations with respect to the desired coding sequence by site-directed mutagenesis are well understood, and the coding sequence can thus be provided with suitable sites for attachment to signal sequence or fusion sequence, or into expression vectors.

If bacterial hosts are chosen, it is likely that the protein will be produced in nonglycosylated form. Modification of the protein produced either intracellularly or as secreted from such bacterial host can be done by providing the polysaccharide substances, by refolding using techniques to sever and reform disulfide bonds, or other post-translational ex vivo processing techniques. If the protein is produced in mammalian or other eucaryotic hosts, the cellular environment is such that post-translational processing can occur in vivo, and a glycosylated form of the protein is produced.

The recombinant cells are cultured under conditions suitable for the host in question, and the protein is recovered from the cellular lysate or from the medium, as determined by mode of expression. Purification of the protein can be achieved using methods similar to that disclosed by Scott, R. W., et al, *J Biol Chem* (supra), or by other means known in the art.

The purified protein is then formulated according to its application. For pharmaceutical applications, the protein is formulated into compositions using standard excipients, as is understood by practitioners of the art, and disclosed, for example, in *Remington's Pharmaceutical Sciences*, latest edition, Mack Publishing Company. If to be used in diagnostic or immunoassay, the protein may be labeled using radioactive species, for example, or fluorescent markers. If it is to be used to obtain antibody preparations, the protein is prepared for injection along with suitable adjuvant. Methods of modifying the recombinant protein of the invention according to its desired use will be clear from the generally practiced techniques of the art.

C. Standard Methods

Most of the techniques which are used to transform cells, construct vectors, extract messenger RNA, prepare cDNA libraries, and the like are widely practiced in the art, and most practitioners are familiar with the standard resource materials which describe specific conditions and procedures. However, for convenience, the following paragraphs may serve as a guideline.

C.1. Hosts and Control Sequences

Both procaryotic and eucaryotic systems may be used to express the FGF encoding sequences; procaryotic hosts are, of course, the most convenient for cloning procedures. Procaryotes most frequently are represented by various strains of *E. coli*; however, other microbial strains may also be used. Plasmid vectors which contain replication sites, selectable markers and control sequences derived from a species compatible with the host are used; for example, *E. coli* is typically transformed using derivatives of pBR322, a plasmid derived from an *E. coli* species by Bolivar, et al, *Gene* (1977) 2:95. pBR322 contains genes for ampicillin and tetracycline resistance, and thus provides multiple selectable markers which can be either retained or destroyed in constructing the desired vector. Commonly used procaryotic control sequences which are defined herein to include promoters for transcription initiation, optionally with an operator, along with ribosome binding site sequences, include such commonly used promoters as the β-lactamase (penicillinase) and lactose (lac) promoter systems (Chang, et al, *Nature* (1977) 198:1056) and the tryptophan (trp) promoter system (Goeddel, et al *Nucleic Acids Res* (1980) 8:4057) and the lambda-derived $P_L$ promoter and N-gene ribosome binding site (Shimatake, et al, *Nature* (1981) 292:128).

In addition to bacteria, eucaryotic microbes, such as yeast, may also be used as hosts. Laboratory strains of *Saccharomyces cerevisiae*, Baker's yeast, are most used although a number of other strains or species are commonly available. Vectors employing, for example, the 2μ origin of replication of Broach, J. R., *Meth Enz* (1983) 101:307, or other yeast compatible origins of replication (see, for example, Stinchcomb, et al, *Nature* (1979) 282:39, Tschumper, G., et al, *Gene* (1980) 10:157 and Clarke, L, et al, *Meth Enz* (1983) 101:300) may be used. Control sequences for yeast vectors include promoters for the synthesis of glycolytic enzymes (Hess, et al, *J Adv Enzyme Reg* (1968) 7:149; Holland, et al, *Biochemistry* (1978) 17:4900). Additional promoters known in the art include the promoter for 3-phosphoglycerate kinase (Hitzeman, et al, *J Biol Chem* (1980) 255:2073). Other promoters, which have the additional advantage of transcription controlled by growth conditions and/or genetic background are the promoter regions for alcohol dehydrogenase 2, isocytochrome C, acid phosphatase, degradative enzymes associated with nitrogen metabolism, the alpha factor system and enzymes responsible for maltose and galactose utilization. It is also believed terminator sequences are desirable at the 3' end of the coding sequences. Such terminators are found in the 3' untranslated region following the coding sequences in yeast-derived genes.

It is also, of course, possible to express genes encoding polypeptides in eucaryotic host cell cultures derived from multicellular organisms. See, for example, Axel, et al, U.S. Pat. No. 4,399,216. These systems have the additional advantage of the ability to splice out introns and thus can be used directly to express genomic fragments. Useful host cell lines include VERO and HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers, et al, *Nature* (1978) 273:113), or other viral promoters such as those derived from polyoma, Adenovirus 2, bovine papilloma virus, or avian sarcoma viruses. The controllable promoter, hMTII (Karin, M., et al, Nature (1982) 299:797–802) may also be used. General aspects of mammalian cell host system transformations have been described by Axel (supra). It now appears, also that "enhancer" regions are important in optimizing expression; these are, generally, sequences found upstream or downstream of the promoter region in non-coding DNA regions. Origins of replication may be obtained, if needed, from viral sources. However, integration into the chromosome is a common mechanism for DNA replication in eucaryotes.

C.2. Transformations

Depending on the host cell used, transformation is done using standard techniques appropriate to such cells. The calcium treatment employing calcium chloride, as described by Cohen, S. N., *Proc Natl Acad Sci (USA)* (1972) 69:2110, or the $RbCl_2$ method described in Maniatis, et al, *Molecular Cloning: A Laboratory Manual*

(1982) Cold Spring Harbor Press, p. 254 and Hanahan, D., *J Mol Biol* (1983) 166:557-580 may be used for procaryotes or other cells which contain substantial cell wall barriers. For mammalian cells without such cell walls, the calcium phosphate precipitation method of Graham and van der Eb, *Virology* (1978) 52:546, optionally as modified by Wigler, M., et al, *Cell* (1979) 16:777-785 may be used. Transformations into yeast may be carried out according to the method of Beggs, J. D., *Nature* (1978) 275:104-109 or of Hinnen, A., et al, *Proc Natl Acad Sci (USA)* (1978) 75:1929.

C.3. Vector Construction

Construction of suitable vectors containing the desired coding and control sequence employs standard ligation and restriction techniques which are well understood in the art. Isolated plasmids, DNA sequences, or synthesized oligonucleotides are cleaved, tailored, and religated in the form desired.

The DNA sequences which form the vectors are available from a number of sources. Backbone vectors and control systems are generally found on available "host" vectors which are used for the bulk of the sequences in construction. Typical sequences have been set forth in ¶C.1 above. For the pertinent coding sequence, initial construction may be, and usually is, a matter of retrieving the appropriate sequences from cDNA or genomic DNA libraries. However, once the sequence is disclosed it is possible to synthesize the entire gene sequence in vitro starting from the individual nucleoside derivatives. The entire gene sequence for genes of sizeable length, e.g., 500-1000 bp may be prepared by synthesizing individual overlapping complementary oligonucleotides and filling in single stranded nonoverlapping portions using DNA polymerase in the presence of the deoxyribonucleotide triphosphates. This approach has been used successfully in the construction of several genes of known sequence. See, for example, Edge, M. D., *Nature* (1981) 292:756; Nambair, K. P., et al, *Science* (1984) 223:1299; Jay, Ernest, *J Biol Chem* (1984) 259:6311.

Synthetic oligonucleotides are prepared by either the phosphotriester method as described by Edge, et al, *Nature* (supra) and Duckworth, et al, *Nucleic Acids Res* (1981) 9:1691 or the phosphoramidite method as described by Beaucage, S. L., and Caruthers, M. H., *Tet Letts* (1981) 22:1859 and Matteucci, M. D., and Caruthers, M. H., *J Am Chem Soc* (1981) 103:3185 and can be prepared using commercially available automated oligonucleotide synthesizers. Kinasing of single strands prior to annealing or for labeling is achieved using an excess, e.g., approximately 10 units of polynucleotide kinase to 1 nmole substrate in the presence of 50 mM Tris, pH 7.6, 10 mM $MgCl_2$, 5 mM dithiothreitol, 1-2 mM ATP, 1.7 pmoles $\gamma$32P-ATP (2.9 mCi/mmole), 0.1 mM spermidine, 0.1 mM EDTA.

Once the components of the desired vectors are thus available, they can be excised and ligated using standard restriction and ligation procedures.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 $\mu$g of plasmid or DNA sequence is cleaved by one unit of enzyme in about 20 $\mu$l of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* (1980) 65:499-560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM $MgCl_2$, 6 mM DTT and 0.1-1.0 mM dNTPs. The Klenow fragment fills in at 5' single-stranded overhangs but chews back protruding 3' single strands, even though the four dNTPs are present. If desired, selective repair can be performed by supplying only one of the, or selected, dNTPs within the limitations dictated by the nature of the overhang. After treatment with Klenow, the mixture is extracted with phenol/chloroform and ethanol precipitated. Treatment under appropriate conditions with S1 nuclease or BAL-31 results in hydrolysis of any single-stranded portion.

Ligations are performed in 15-50 $\mu$l volumes under the following standard conditions and temperatures: for example, 20 mM Tris-Cl pH 7.5, 10 mM $MgCl_2$, 10 mM DTT, 33 $\mu$g/ml BSA, 10 mM-50 mM NaCl, and either 40 $\mu$M ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 33-100 $\mu$g/ml total DNA concentrations (5-100 nM total end concentration). Intermolecular blunt end ligations are performed at 1 $\mu$M total ends concentration.

In vector construction employing "vector fragments", the vector fragment is commonly treated with bacterial alkaline phosphatase (BAP) or calf intestinal alkaline phosphatase (CIP) in order to remove the 5' phosphate and prevent self-ligation of the vector. Digestions are conducted at pH 8 in approximately 10 mM Tris-HCl, 1 mM EDTA using about 1 unit of BAP or CIP per $\mu$g of vector at 60° for about one hour. In order to recover the nucleic acid fragments, the preparation is extracted with phenol/chloroform and ethanol precipitated. Alternatively, religation can be prevented in vectors which have been double digested by additional restriction enzyme digestion and separation of the unwanted fragments.

For portions of vectors derived from cDNA or genomic DNA which require sequence modifications, site specific primer directed mutagenesis may be used (Zoller, M. J., and Smith, M. *Nucleic Acids Res* (1982) 10:6487-6500 and Adelman, J. P., et al, *DNA* (1983) 2:183-193). This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting partially or fully double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are washed after hybridization with kinased synthetic primer at a wash temperature which permits binding of an exact match, but at which the mismatches with the original strand are sufficient to prevent binding. Plaques which hybridize with the probe are then picked, cultured, and the DNA recovered.

C.4. Verification of Construction

For confirmation of vector construction, or for other sequencing, DNA is first amplified and isolated. The isolated DNA is analyzed by restriction and/or sequenced by the dideoxy nucleotide method of Sanger, F., et al, *Proc Natl Acad Sci (USA)* (1977) 74:5463 as further described by Messing, et al, *Nucleic Acids Res* (1981) 9:309, or by the method of Maxam, et al, *Methods in Enzymology* (1980) 65:499.

C.5. Host Exemplified

Host strains used in cloning and procaryotic expression herein are as follows:

For cloning and sequencing, and for expression of construction under control of most bacterial promoters, *E. coli* strain MM294 is used. For mammalian expression, COS-7 or CHO cells are employed.

EXAMPLES

The following example is intended to illustrate but not to limit the invention. In one aspect, the examples detail a method to retrieve the desired cDNA sequences; however, this process need not be repeated. A partial DNA sequence for the PN clone is given in FIG. 3, and standard synthetic methods may be used to construct either this precise sequence or the equivalent degenerate sequence employing alternate codons. Synthesis of DNA sequence of this length are by now nearly routine in the art. See, for example, Edge et al, *Nature* (1981) 292:756. In addition, on 4 June 1986, applicants have deposited at the American Type Culture Collection, Rockville, Md. the PN-18 clone in phage γgt10 having ATCC No. 40238. This contains the relevant coding sequence, which can be manipulated starting from the physical substance.

EXAMPLE 1

Purification of Native Protease Nexin-I

PN-I was prepared from serum-free conditioned medium, as described in Scott, R. W., et al. *J Biol Chem* (1985) (supra). Briefly, the harvested medium was filtered through a 45μ millipore filter, and the proteins concentrated by Amicon hollow fiber filtration. The concentrated medium from a single 3 1² microcarrier culture was passed over a 0.7×30 cm heparin-agarose column, preequilibrated in 0.3M sodium chloride in phosphate buffer, and eluted with 1.0M sodium chloride in phosphate buffer, both containing 0.02% sodium azide. Elution was obtained in 0.55-0.6M NaCl. The PN-I-containing fractions were concentrated by dialysis and then subjected to gel-exclusion chromatography by dialyzing 1-2 mg PN-I in 1 ml into column buffer containing 0.5M NaCl, and applied to a 1×60 cm Biogel P-100 (Biorad 100-200 mesh) column and eluted with column buffer. The peak fractions were concentrated to 1 ml and stored at −80° C. The amino acid sequence and sugar composition were determined on this purified material.

The N-terminal amino acid sequence for the first 34 amino acids was determined with the results set forth above.

EXAMPLE 2

Isolation of Protease Nexin I cDNA

Human foreskin fibroblasts were grown to confluence in 30×150 mm flasks, as described by Scott, R. W., *J Biol Chem* (1983) 258:10439, yielding approximately 5×10⁸ cells. Twenty-four hr prior to harvest, cells were refed to stimulate the production of PN-I mRNA. The cells were harvested in the cold and washed twice with phosphate buffered saline (PBS). The cell pellets were recovered, homogenized in buffer containing 20 mM vanadyl complex, and 0.2% Nonidet P-40 detergent, and then centrifuged for 10 min at 14,000 rpm. RNA was prepared from the supernatant using phenol/chloroform extraction and the total RNA obtained was subjected to oligo-dT affinity chromatography to obtain mRNA.

Figure 1A:
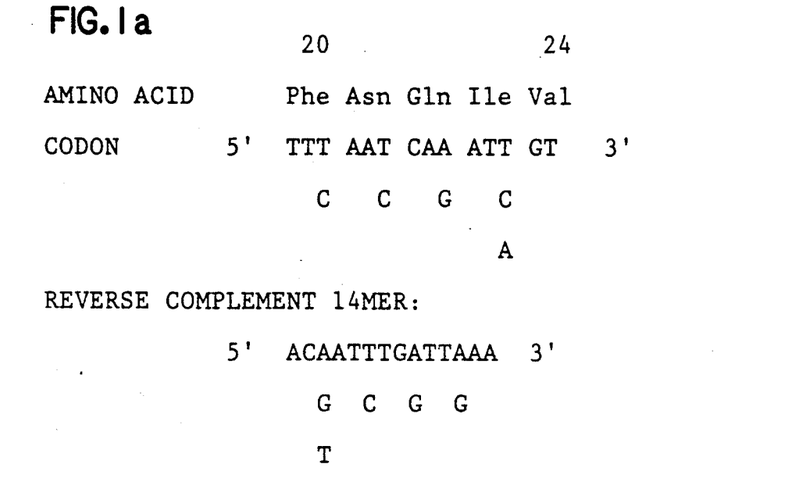
FIGS. 1a and 1b show the sequences of two probe mixtures which were employed to identify PN-I clones.
Figure 1B:
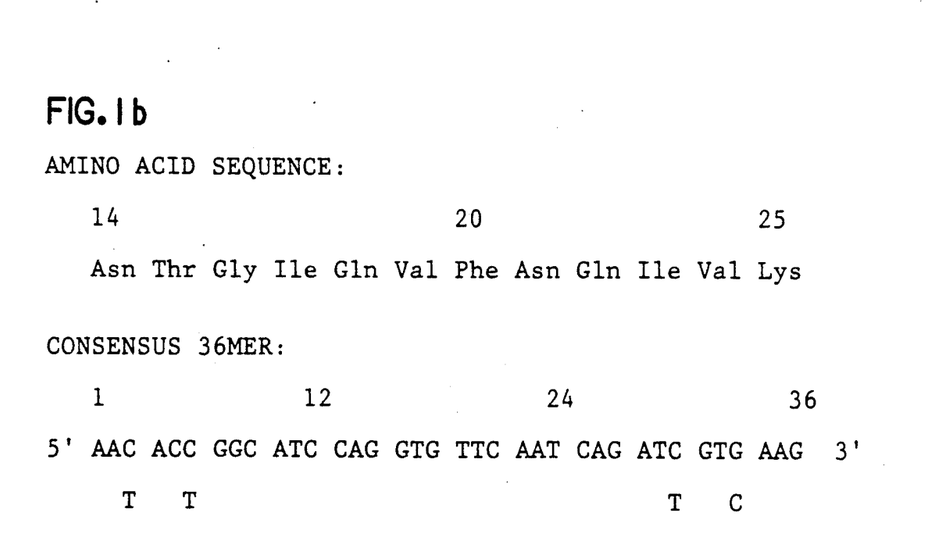

The isolated messenger was gel fractionated and probed with a mixture of twenty-four 14-mers having the sequence shown in FIG. 1a, which is the reverse complement of DNA encoding amino acids 20-24 of the determined N-terminal sequence. The probe hybridizes to mRNA of approximately 2500-2700 nucleotides in length.

The total mRNA preparation was then used as a template to prepare a cDNA library in γgt10, substantially as described by Hunyh, T. V., et al, *DNA Cloning Techniques: A Practical Approach* (1984), Glover, D., ed, IRL, Oxford, but with second-strand synthesis performed according to the method of Gubler, V., et al, *Gene* (1983) 25:263-269. The resulting cDNA was cut with EcoRI and inserted into the EcoRI site of γgt10, as described by Hunyh et al (supra). Several million phage plaques were obtained and triplicate filter lifts were prepared. Plaques were duplicate screened under conditions of moderate stringency (6×SSC at 30° C.), with the 5' end ³²P-ATP-labeled mixture of the 14-mers above. This resulted a number of positive clones. Of the 60 clones picked and cultured. 48 of them also hybridized under comparably stringent conditions to a 36-nucleotide oligomer of the sequence shown in FIG. 1b, which was a consensus sequence designed on the basis of amino acids 14-25, the sequence determined in the native protein.

Figure 2:
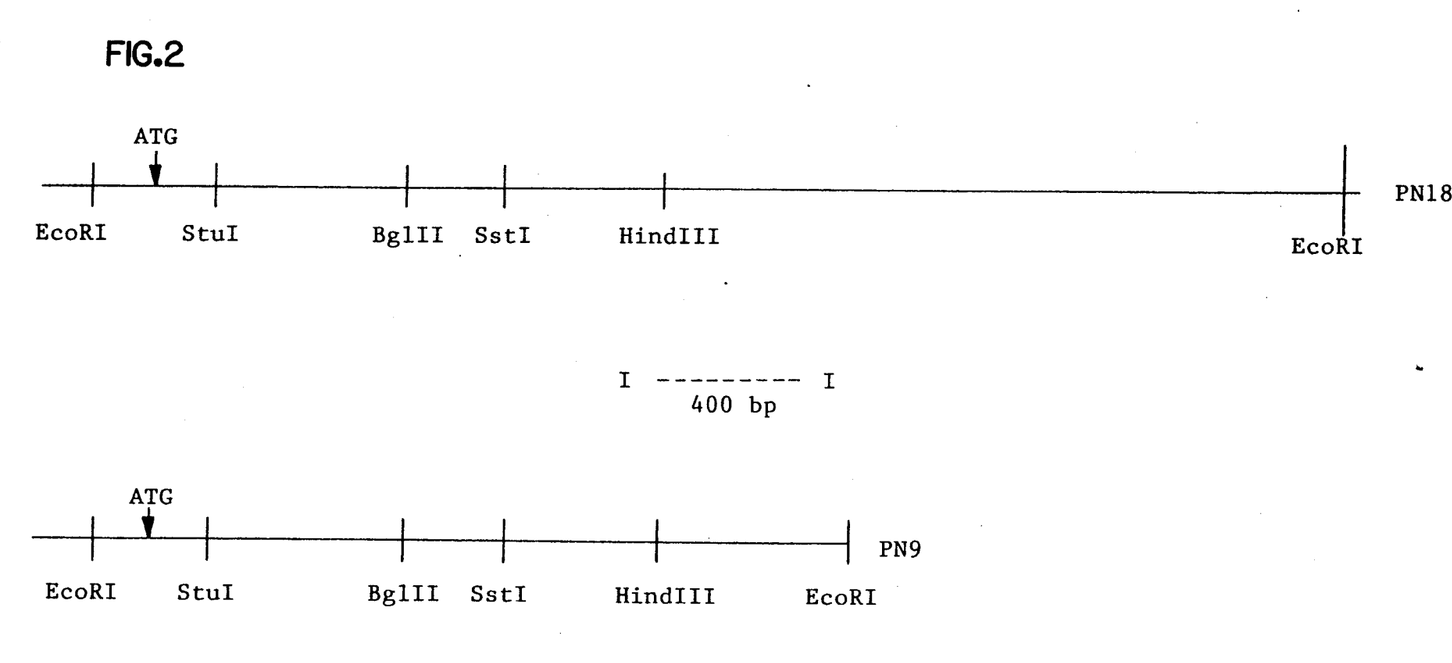
FIG. 2 shows the restriction map of the cDNA clones designated PN-9 and PN-18, each of which contains the coding sequence for the complete PN-I protein.

Fifteen of these 48 clones were of approximately the size expected from the mRNA to be of sufficient length to encode the entire sequence. These fell into two classes by size: 2000 bp and 3000 bp. One 3000 bp clone was designated PN-18, and one 2000 bp clone was designated PN-9. These clones have identical coding sequences. Restriction maps show them to include the 5' end of the gene; these maps are shown in FIG. 2.

PN-18 was restricted with Sau3A and cloned into the BamHI site of M13. To confirm the presence of the correct cDNA, the resulting M13 subclones were screened with the 14-mer mixture and a 55 bp fragment containing the oligomer sequence encoding amino acids 17-34 of the native protein was verified; this sequence is included as the overlined sequence in FIG. 3.

Figure 3:
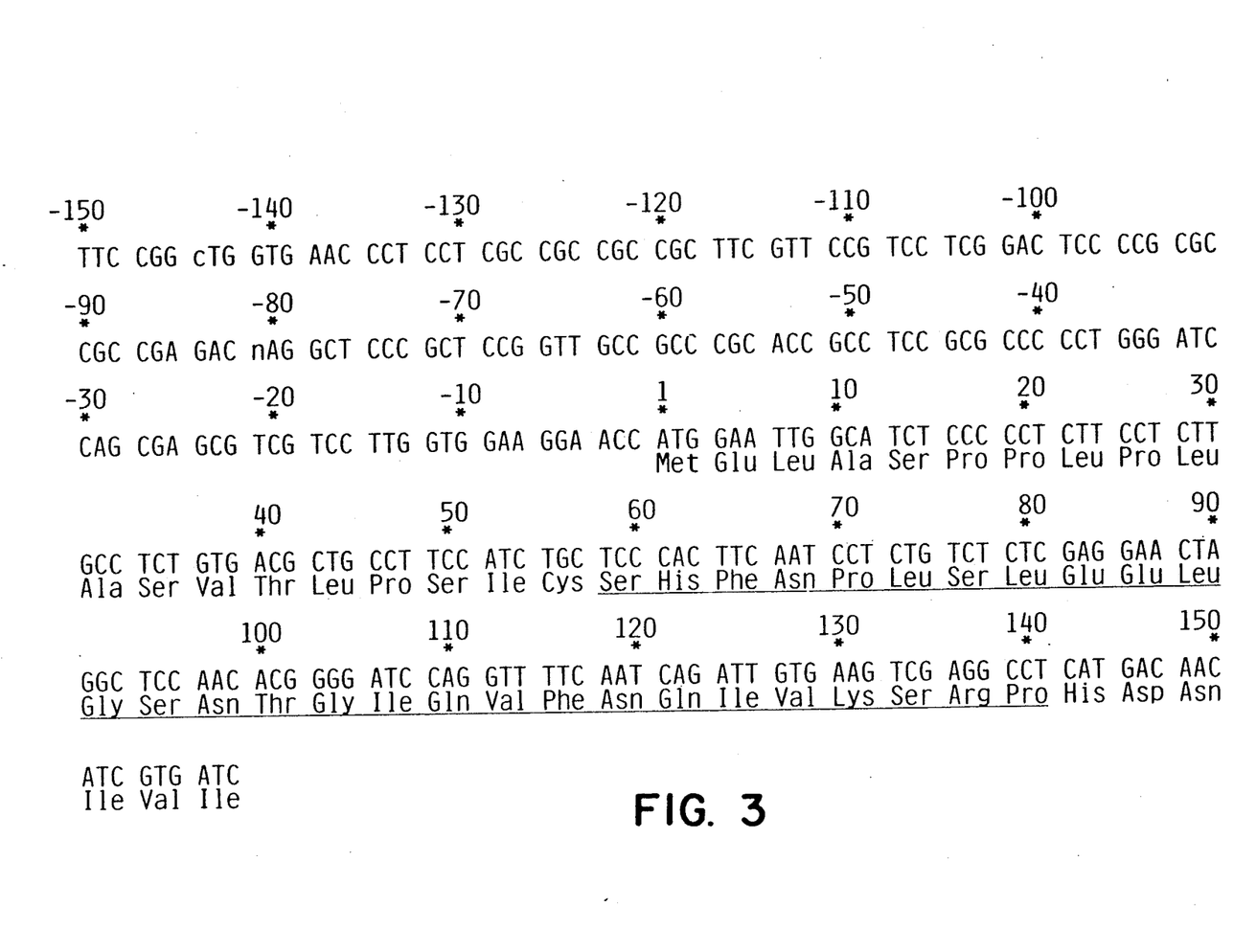
FIG. 3 shows the partial oligonucleotide sequence of PN-18 along with the deduced amino acid sequence; it also includes the sequence determined for a 55 bp Sau3A fragment thereof.

Thirteen of the above 15 clones contained a 750 bp EcoRI-BglII fragment which hybridizes to the 14-mer probe and is believed to encode the 5' portion of the gene. This segment has been partially sequenced, and the results are shown in FIG. 3. The determined sequence icludes the 55 bp Sau3A fragment above, and the codons for the N-terminal sequence determined above, as well as codons for a putative signal sequence extending back to an ATG. The entire PN-18 clone, of approximately 3000 bp, is deposited with the American Type Culture Collection, and contains the complete PN-I sequence.

Figure 4:
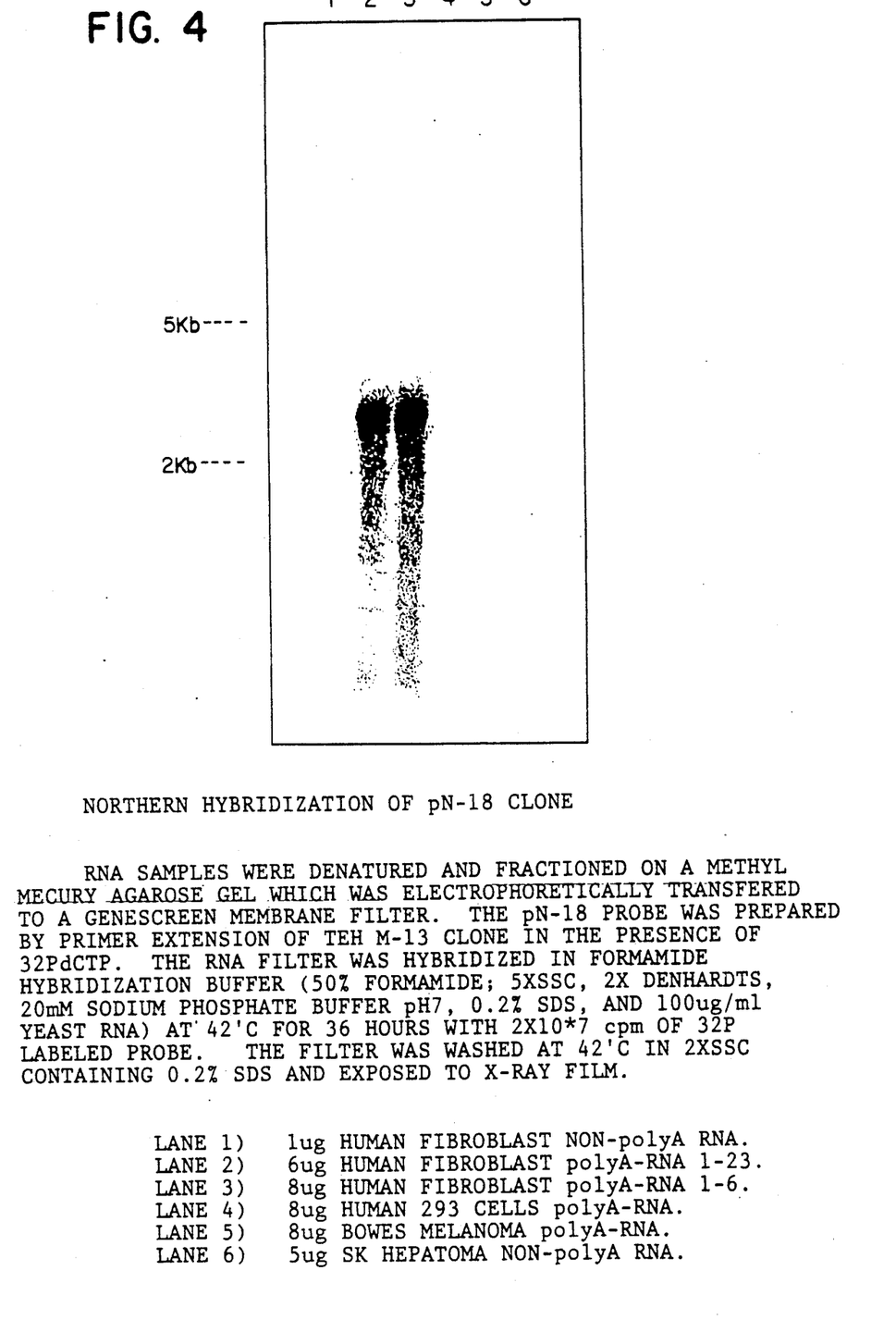
FIG. 4 shows a Northern blot of mRNA extracts from several cell lines using a Sau3A fragment from PN-18 as a probe.

Identification of PN-18 with PN-I production was verified by Northern blot, as shown in FIG. 4. The 55 bp Sau3A fragment obtained from PN-18 was labeled and used to probe mRNA obtained from human foreskin fibroblasts and from several other cell lines not capable of PN-I production. The probe hybridizes only to the mRNA of about 2.8 kb from the PN-I-producing cells.

EXAMPLE 3

Murine PN-I cDNA

In a manner similar to that described in Example 2, a cDNA library prepared in γgt10 from mRNA extracted from mouse fibroblasts is screened with the 55 bp Sau3A fragment derived from PN-18. Phage hybridizing to this probe are then picked and cloned to obtain the desired murine PN-I cDNA.

EXAMPLE 4

Construction of Expression Vectors

The entire EcoRI cassette from PN-9 or PN-18 is ligated into the host expression vector pFD11 (Simonsen, C C, et al, *Proc Natl Acad Sci* USA (1983) 80:2495-2499) under control of the SV40 early promoter. pFD11 is digested with HindIII and XhoI, blunted, and ligated to the blunted EcoRI cassette, and the ligation mixture used to transform *E. coli* MM294 for amplification. Plasmid DNA is then transfected into COS-7 cells for transient expression, or into CHO cells, which are then cultured for the production of PN-I.

What is claimed is:

1. A method to purify native protease nexin 1 (PN-I), which method comprises:

applying a medium containing PN-I to a column containing heparin bound to solid support, said column being preequilibrated, eluting said column with a gradient of 0.3-1M NaCl to obtain fractions, recovering the fractions containing classes of PN-I, followed by subjecting said fractions to gel exclusion chromatography using a gel with an exclusion of 100 kd.

2. The method of claim 1 wherein the heparin is bound to agarose support.

3. The method of claim 1 wherein the PN-I-containing medium is serum-free medium conditioned by human foreskin fibroblasts.

4. The method of claim 3 wherein the fibroblasts are grown in microcarrier culture.

5. The method of claim 1 wherein the column is preequilibrated with a solution comprising 0.3M NaCl.

* * * * *